United States Patent [19]

Cook

[11] Patent Number: 4,637,396

[45] Date of Patent: Jan. 20, 1987

[54] BALLOON CATHETER

[75] Inventor: William A. Cook, Bloomington, Ind.

[73] Assignee: Cook, Incorporated, Bloomington, Ind.

[21] Appl. No.: 665,374

[22] Filed: Oct. 26, 1984

[51] Int. Cl.$^4$ ............................................. A61M 29/02
[52] U.S. Cl. ...................................... 128/344; 604/99; 604/102; 604/103
[58] Field of Search ...................... 128/344, 343, 348.1, 128/341, 207.15, 325; 604/96, 104, 107, 97, 98, 604/99, 100, 101, 102, 103'

[56] References Cited

U.S. PATENT DOCUMENTS

| 2,213,144 | 8/1940 | McAdams | 66/172 E |
| 3,435,826 | 4/1969 | Fogarty | 128/344 |
| 4,362,150 | 12/1982 | Lombardi, Jr. | 604/99 |
| 4,516,972 | 5/1985 | Samson | 604/282 |

FOREIGN PATENT DOCUMENTS 1566674 5/1980 United Kingdom .

Primary Examiner—Robert P. Swiatek
Assistant Examiner—Cary E. Stone
Attorney, Agent, or Firm—Woodard, Weikart, Emhardt & Naughton

[57] ABSTRACT

A balloon catheter having an expandable and collapsible elastic balloon is shown, wherein the balloon is reinforced by knitted fabric such that the balloon can not expand beyond a predetermined diameter regardless of the internal pressure applied to the balloon. The knitted construction permits the balloon to expand in diameter without shortening in length, and permits the balloon to collapse smoothly without folds and wrinkles.

15 Claims, 6 Drawing Figures

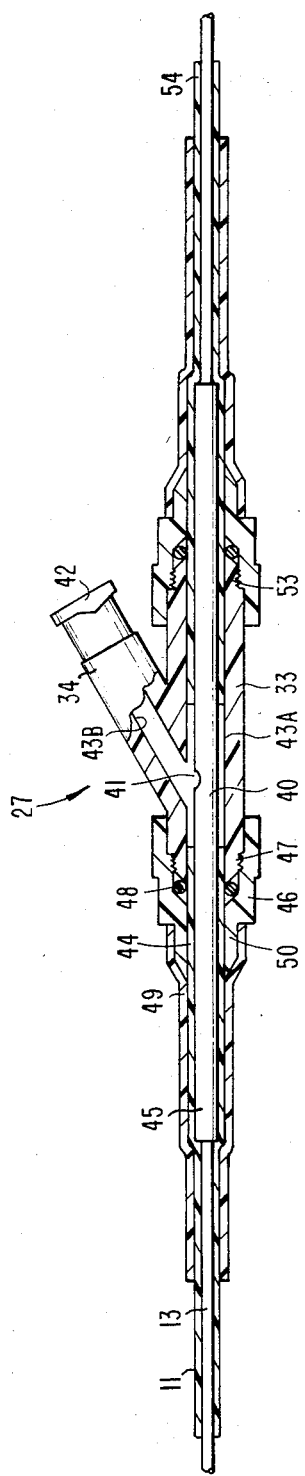
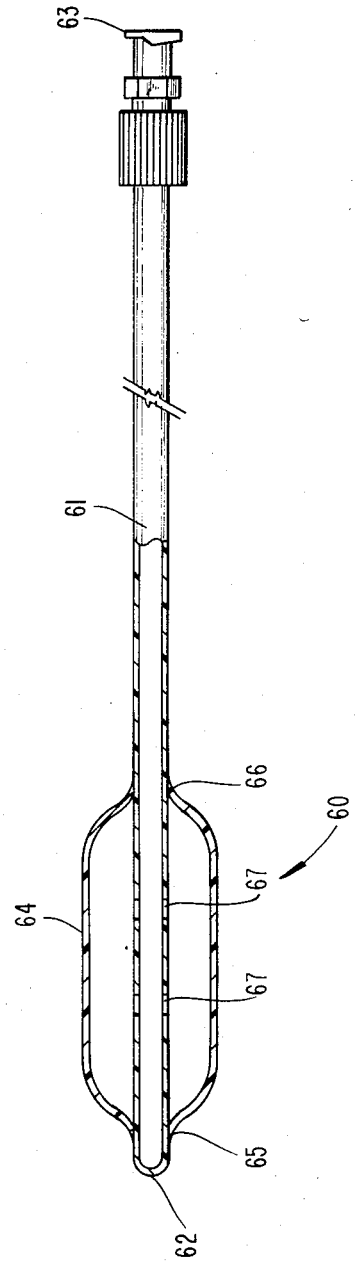
Fig.5
Fig.6

BALLOON CATHETER

BACKGROUND OF THE INVENTION

1. Field of the Invention

This invention relates in general to catheters having inflatable balloons and in particular to a balloon catheter wherein the balloon is fabric reinforced.

2. Background of the Prior Art

Catheters having inflatable balloons affixed thereto are used in a variety of applications. One application for a balloon catheter is as a dilator for blood vessels which have been partially or entirely blocked by deposits on the inside wall of the blood vessel. The catheter is introduced into the affected blood vessel and the deflated balloon is maneuvered into the blocked area. By inflating the balloon, the deposits are compressed against the wall of the blood vessel, thereby opening the blood vessel to blood flow.

Because of the danger of over dilating and thereby bursting the blood vessel, it is preferred that the balloon be reinforced so that it can expand only to a predetermined maximum diameter regardless of the interior pressure applied. One balloon catheter which is so reinforced is described in British Pat. No. 1,566,674 to Hanecka and Olbert. The Hanecka balloon is reinforced by a woven synthetic fabric wherein the filaments of the fabric extend along helices of opposite sense. As stated in the patent, such a reinforced balloon shortens in length with an increase in diameter. Therefore, to prevent folds in the balloon when it is deflated, the Hanecka device employs two coaxial tubes, one slidable within the other, for lengthening the balloon when it is deflated and permitting shortening of the balloon as it is inflated. One disadvantage of such a balloon catheter is that the structure requires components or parts which are movable relative to one another.

The present invention provides a reinforced inflatable balloon which is smooth in its deflated state, yet expands in diameter without decreasing in length.

SUMMARY OF THE INVENTION

A balloon catheter includes a catheter tube having an expandable and collapsible balloon attached thereto. Means are provided for connecting the balloon to an external source of pressurized fluid. The balloon includes an impervious elastic wall for retaining pressure therein, the balloon being reinforced by a knitted fabric layer to limit the maximum expanded diameter of the balloon.

It is an object of the present invention to provide an improved balloon catheter which is reinforced to limit its maximum expanded diameter, yet which has a smooth configuration in both its contracted and expanded states.

It is another object to provide a balloon catheter as described above with a minimum of moving parts.

Further objects and advantages will become apparent from the following description.

BRIEF DESCRIPTION OF THE DRAWINGS

FIG. 5 is an enlarged longitudinal sectional view of the Y-fitting of the balloon catheter of FIG. 1.

FIG. 6 is a side elevational view of an alternative embodiment of a balloon catheter constructed in accordance with the present invention.

DESCRIPTION OF THE PREFERRED EMBODIMENT

Figure 1:
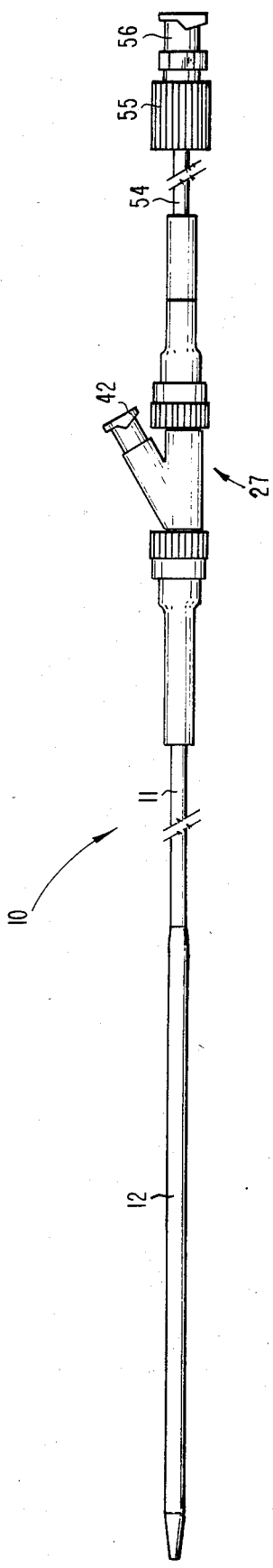
FIG. 1 is a side elevational view of a balloon catheter constructed in accordance with the present invention.
Figure 2:
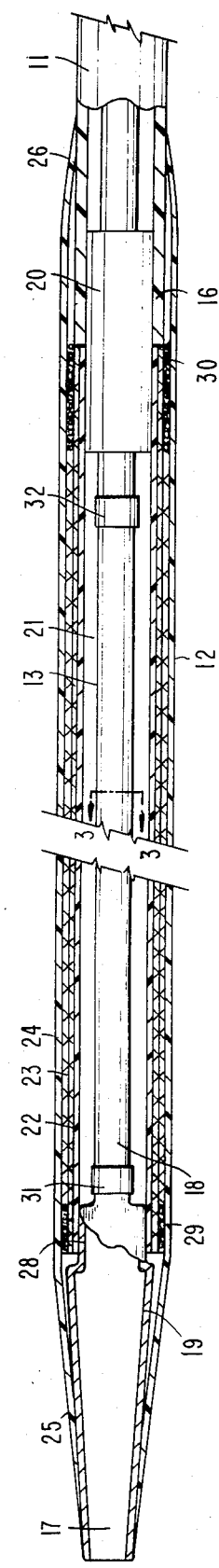
FIG. 2 is an enlarged view of the balloon of the balloon catheter of FIG. 1, with portions shown in longitudinal section.
Figure 3:
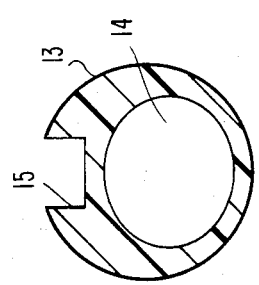
FIG. 3 is an enlarged cross sectional view of the inner member of the balloon catheter of FIG. 1 taken along the line 3—3 of FIG. 2.

Referring in particular to FIGS. 1 and 2, there is illustrated a balloon catheter 10 including a catheter tube 11 made of radiopaque flexible urethane tubing. Attached to the distal end portion of catheter tube 11 is an inflatable and collapsible balloon 12, which is shown in greater detail in FIG. 2. Disposed coaxially within catheter tube 11 and balloon 12 is a flexible inner member 13. FIG. 3 shows a cross sectional view of inner member 13, which includes an interior eccentrically located lumen 14 and a longitudinal groove 15. Groove 15 aids in providing a longitudinal passageway between inner member 13 and catheter tube 11 for the passage of fluid therethrough for inflating balloon 12, as described below.

Referring to FIG. 2, it can be seen that inner member 13 extends beyond the distal end 16 of catheter tube 11. Attached to the distal end 18 of inner member 13 is a hollow open tapered plastic tip 19. Lumen 14 is in communication with opening 17 in tip 19. Affixed within the distal end 16 of catheter tube 11 and extending therefrom is a thin-walled stainless steel sleeve 20. Balloon 12 is disposed coaxially about inner member 13 between sleeve 20 and tip 19, defining an annular balloon chamber 21. Balloon 12 includes a three layer wall, the inner layer 22 being an elastic impervious urethane membrane for retaining pressure within balloon chamber 21, the middle layer 23 being a knitted fabric tube, and the outer layer 24 being an elastic impervious urethane membrane, the ends of which are tapered at points 25 and 26 to a smooth transition with the outer surfaces of plastic tip 19 and catheter tube 11. Inner layer 22 and middle layer 23 are secured to portion 28 of tip 19 by tiedown thread 29 which is wound tightly about middle layer 23. Similarly, inner layer 22 and middle layer 23 are secured to sleeve 20 by tiedown thread 30. Outer layer 24 is preferably formed by dipping partially completed balloon 12, including inner layer 22 and middle layer 23, into a liquid urethane solution. Radiopaque marker bands 31 and 32 are disposed about inner member 13 proximate the ends of the inflatable portion of the balloon to aid in the placement of the balloon at the desired location within a blood vessel.

Figure 4:
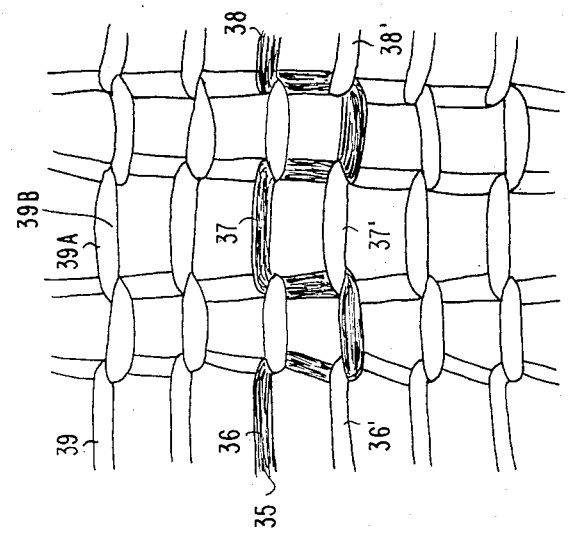
FIG. 4 is an enlarged view of the knitted fabric reinforcement layer of the balloon of the balloon catheter of FIG. 1., shown in its expanded state.

Referring to FIG. 4, there is shown in detail the configuration of a portion of knitted middle layer 23 in an expanded state. Middle layer 23 is knitted as a tube from a single yarn strand arranged generally in a helix, with each turn of the helix comprising a successive row of knitting. Machines for knitting tube shaped fabric are commercially available, with the number of needles varying depending on the size of tube being knitted. The prototype embodiment described herein was knitted on a craft or hobby type machine to which a few needles and an electric motor were added. Preferably, during fabrication of balloon 12, middle layer 23 is knitted over preformed inner layer 22. As is characteristic of knitted fabric, each row is configured as a series of periodically spaced loops, with each loop in each row passing through an adjacent loop in the next preceding row. To illustrate this knit stitch, one row 35 in FIG. 4 is shown darker. Row 35 includes a series of loops, such as loops 36, 37 and 38, each of which passes through loops 36', 37' and 38', respectively, of the next preceding row.

The yarn strand 39 of which middle layer 23 is knitted is comprised of multiple plies or filaments. In the preferred embodiment, the yarn strand is comprised of two parallel twisted plies, one ply 39A being strong and inelastic for limiting the maximum expanded diameter of the balloon, and the other ply 39B being elastic for contracting the balloon when inflation pressure is absent. Preferably, the strong inelastic ply is made of Kevlar, a DuPont product, although it can also be made of other known natural or synthetic fibers, such as Dacron, but with a decrease in the bursting strength of the balloon. The elastic ply is preferably made of a material known by the trade name Spandex.

Middle layer 23 is knitted loosely with the Spandex plies being stretched during knitting so that after the tube is knitted, the Spandex strands contract and collapse middle layer 23 into its normal configuration. Thereafter, when balloon 12 is expanded, knitted middle layer 23 expands in diameter until all of the loops are pulled taut (as shown in FIG. 4), at which point knitted layer 23 will expand no further because of the inelastic nature of the Kevlar plies. If additional inflation pressure be applied after balloon 12 reaches its predetermined maximum diameter, no further increase in diameter will be observed unless the pressure is so great that the tension in the yarn exceeds the tensile strength of the Kevlar plies, at which point the balloon would burst. Of course, in the normal use of the present device it would never be inflated to the point of bursting because of the harm that would result to the patient. The physician will realize when the balloon is fully inflated because the pressure of the inflating fluid will begin to rise sharply at that point. It is to be understood that the ratio of maximum to minimum diameter of balloon 12 is determined primarily by how loosely middle layer 23 is originally knitted.

One advantage of a balloon reinforced with a knitted fabric over prior known fabric reinforced balloons is in the expansion and contraction characteristics. Prior known balloons reinforced with a braided or woven fabric tube are unable to expand in diameter without correspondingly decreasing in length. However, a balloon reinforced with the knitted fabric tube described herein is capable of expanding three-dimensionally such that an increase in diameter does not require a decrease in length of the balloon. Consequently, balloon catheter 10 is constructed so that inner member 13 and catheter tube 11 are fixed against relative longitudinal displacement. Balloon 12 is therefore of fixed length. When balloon 12 is collapsed, the fabric of middle layer 23 contracts uniformly such that in the normal unexpanded state the balloon walls are smooth and free from folds and wrinkles.

Referring to FIGS. 1 and 5, there is shown attached to the proximal end portion of catheter 10 a Y-fitting 27 having a main portion 33 and a side branch 34. Bore 43A in main portion 33 communicates with bore 43B in side branch 34. Side branch 34 is terminated in a female Luer lock connector 42 in communication with bore 43B. Disposed within bore 43A is a stainless steel cannula sleeve 40 having a side aperture 41 in alignment with bore 43B of side branch 34. Inner member 13 is disposed within cannula sleeve 40 such that groove 15 is aligned with side aperture 41 and bore 43B. Groove 15 aids in providing a continuous longitudinal passageway from bore 43B to annular balloon chamber 21. Cannula sleeve 40 extends beyond main portion 33 at both ends. The proximal end 44 of catheter tube 11 is expanded to frictionally fit over end 45 of cannula sleeve 40, with proximal end 44 extending within bore 43A. Cap 46 is threadedly received over end portion 47 of Y-fitting 27 with O-ring 48 compressed between cap 46 and end portion 47. O-ring 48 when compressed forms a pressure seal between catheter tube 11 and end portion 47 of Y-fitting 27. Heat shrink tubing 49 is shrunk over extension 50 of cap 46 and the proximal end portion 44 of catheter tube 11 to provide structural reinforcement and further sealing.

At the proximal end 53 of main portion 33 is a secondary catheter tube 54 attached in a manner similar to the attachment of catheter tube 11 to end 47. Referring to FIG. 1, the proximal end of tube 54 is terminated in a cap 55 having a female Luer lock connector 56 in communication with lumen 14 of inner member 13. Inner member 13 and secondary catheter tube 54 are sealed together within cap 55 to prevent relative longitudinal displacement between them.

In its normal configuration, balloon 12 is only slightly greater in diameter than catheter tube 11. In this configuration, the outer surface of balloon 12 is smooth, thus facilitating placement of the balloon within a blood vessel with a minimum of trauma. After balloon 12 has been positioned in the desired location, it is inflated by introducing a saline solution under pressure at the proximal end of catheter 10 through Luer lock connector 42 of side branch 34 such that it flows through bore 43B and aperture 41, and through the longitudinal passageway between catheter tube 11 and inner member 13 (aided by groove 15) into annular balloon chamber 21. Balloon 12 then expands to its predetermined maximum diameter.

Lumen 14 within inner member 13 is externally accessible through Luer lock connector 56 at the proximal end of the catheter assembly, and provides a continuous passageway to the distal opening 17 beyond balloon 12. This passageway is completely independent of the inflation state of balloon 12 and may be used for the introduction of drugs or radiopaque dye into the blood stream.

Referring to FIG. 6, there is illustrated an alternative embodiment of the present invention. Balloon catheter 60 includes a hollow radiopaque urethane catheter tube 61 which is closed at distal end 62. Attached to the proximal end of catheter tube 61 is a female Luer lock connector 63 in communication with the bore of catheter tube 61. Disposed coaxially about the distal end portion of catheter tube 61 is a balloon 64 which is attached and sealed to catheter tube 61 at points 65 and 66 by means similar to that used to secure balloon 12 to tip 19 and sleeve 20 in the previously described embodiment. Likewise, balloon 64 is a three-layer knitted fabric reinforced balloon similar to balloon 12. In the present embodiment, the catheter tube has only one fluid passageway which communicates with the interior of balloon 64 via apertures 67 in catheter tube 61. Balloon 61 can be inflated by pressurized saline solution introduced into catheter tube 61 through Luer lock connector 63.

While particular embodiments of the invention have been illustrated and described in detail in the drawings and foregoing description, it is to be understood that this description is made only by way of example and not as a limitation to the scope of the invention which is claimed below.

The invention claimed is:

1. A balloon catheter, comprising:
   a hollow flexible catheter tube;
   a flexible inner member disposed coaxially within said catheter tube and fixed thereto against relative longitudinal displacement, the distal end of said inner member extending beyond the distal end of said catheter tube, said inner member being sized and configured to provide a longitudinal passageway between said inner member and said catheter tube for the passage of fluid therethrough;
   connecting means for connecting the longitudinal passageway to an external source of pressurized fluid; and
   a balloon disposed coaxially about said inner member, the proximal end of said balloon being fixed and sealed to the distal end of said catheter tube and the distal end of said balloon being fixed and sealed to the distal end of said inner member to define an annular balloon chamber, said annular balloon chamber being in fluid flow communication with the longitudinal passageway, said balloon including an impervious elastic wall for retaining pressure therein, said elastic wall being reinforced by a knitted fabric tube for permitting said balloon to expand to a predetermined maximum diameter while remaining fixed in length.

2. The balloon catheter of claim 1, wherein said knitted fabric tube includes a continuous yarn strand arranged generally in a helix, said yarn being configured as periodically spaced loops, with each loop in each turn of the helix passing through an adjacent loop in the next preceding turn.

3. The balloon catherter of claim 2, wherein the continuous yarn strand includes a plurality of parallel plies, at least one of said plies being elastic and at least one of said plies being strong and inelastic.

4. The balloon catheter of claim 3, wherein said elastic ply is made of Spandex, and said inelastic ply is made of Kevlar.

5. The balloon catheter of claim 3, wherein said flexible inner member includes a longitudinal groove therein for aiding in providing the longitudinal passageway.

6. The balloon catheter of claim 5, wherein said connecting means includes a Luer lock connector.

7. The balloon catheter of claim 5, and further including a lumen within said flexible inner member providing a passageway from the distal end to the proximal end of said balloon catheter.

8. A balloon catheter, comprising:
   a hollow flexible catheter tube;
   connecting means for connecting said catheter tube to an external source of pressurized fluid;
   an expandable and collapsible balloon disposed coaxially about said catheter tube, the ends of said balloon being fixed and sealed to said catheter tube to define an annular balloon chamber, said balloon including an impervious elastic wall for retaining pressure therein, said elastic wall being reinforced by a knitted fabric tube for permitting said balloon to expand to a predetermined maximum diameter while remaining fixed in length; and
   means for providing pressurized fluid flow communication between said catheter tube and said annular balloon chamber.

9. The balloon catheter of claim 8, wherein said means for providing fluid flow communication includes an aperture through the wall of said catheter tube.

10. The balloon catheter of claim 8, wherein said knitted fabric tube includes a continuous yarn strand arranged generally in a helix, said yarn strand being configured as periodically spaced loops, with each loop in each turn of the helix passing through an adjacent loop in the next preceding turn.

11. The balloon catheter of claim 10, wherein the continuous yarn strand includes a plurality of parallel plies, at least one of said plies being elastic and at least one of said plies being strong and inelastic.

12. The balloon catheter of claim 11, wherein said elastic ply is made of Spandex, and said inelastic ply is made of Kevlar.

13. The balloon catheter of claim 11, wherein said connecting means includes a Luer lock connector.

14. A balloon catheter, comprising:
   a catheter tube;
   an expandable and collapsible balloon attached to said catheter tube, said balloon including an impervious elastic layer for retaining pressure therein, said balloon being reinforced by a knitted fabric layer configured as a tube including a continuous yarn strand arranged generally in a helix, said yarn strand being configured as periodically spaced loops, with each loop in each turn of the helix passing through an adjacent loop in the next preceding turn, to limit the maximum expanded diameter of said balloon; and
   means for connecting said balloon in communication with an external source of pressurized fluid.

15. The balloon catheter of claim 14, wherein the continuous yarn strand includes a plurality of parallel plies, at least one of said plies being elastic and at least one of said plies being strong and inelastic.

* * * * *